United States Patent [19]

Sweeney

[11] Patent Number: 5,210,363
[45] Date of Patent: May 11, 1993

[54] HYDROUS ZIRCONIUM OXIDE DEHYDRATION CATALYST

[75] Inventor: William A. Sweeney, Larkspur, Calif.

[73] Assignee: Chevron Research and Technology Company, San Francisco, Calif.

[21] Appl. No.: 852,871

[22] Filed: Mar. 17, 1992

Related U.S. Application Data

[62] Division of Ser. No. 542,278, Jun. 22, 1990, Pat. No. 5,130,287.

[51] Int. Cl.$^5$ .................................................. C07C 1/24
[52] U.S. Cl. .................................... 585/640; 585/639; 502/349
[58] Field of Search ................. 585/639, 640; 502/349

[56] References Cited

U.S. PATENT DOCUMENTS

| | | | |
|---|---|---|---|
| 4,681,979 | 7/1987 | Araki et al. | 585/639 |
| 5,059,734 | 10/1991 | Sweeney | 585/639 |
| 5,130,287 | 7/1992 | Sweeney | 502/349 |

*Primary Examiner*—Anthony Mc Farlane
*Attorney, Agent, or Firm*—R. J. Sheridan; T. G. DeJonghe

[57] ABSTRACT

Disclosed is a hydrous zirconium oxide catalyst for the dehydration of alcohols of the general formula $$R-\underset{\underset{\displaystyle }{|}}{\overset{\overset{\displaystyle OH}{|}}{CH}}-CH_3$$

to terminal olefins, as well as a method for preparing said catalyst. The catalyst provides high conversion of alcohol to olefin, high dehydration selectivity, and high selectivity for terminal olefin.

4 Claims, No Drawings

HYDROUS ZIRCONIUM OXIDE DEHYDRATION CATALYST

This is a divisional of application Ser. No. 542,278, filed Jun. 22, 1990 now U.S. Pat. No. 5,130,287.

BACKGROUND OF THE INVENTION

1. Field of the Invention

The present invention relates to a hydrous zirconium oxide dehydration catalyst and a method for producing a compound having a double bond at the terminal position (hereinafter referred to as a "terminal olefin" or "α-olefin") using such a catalyst.

2. Description of the Prior Art

The present invention relates to a method for producing a terminal olefin. More particularly, the present invention relates to a method for producing the terminal olefin by dehydration of a compound represented by the formula (I)

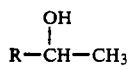
(I)

wherein R is a $C_2$–$C_{20}$ hydrocarbon group which may have one or more double bonds.

It is hitherto well known that an olefin can be produced by dehydration of a compound represented by the formula (I). The details of the method can be taken, for example, from J. Am. Chem. Soc., 85, 2180 (1963), or from Oil Chemistry, 17, 236 (1968) It is also known from DE-A-144 362 and the corresponding CH-A-721077 that zirconium oxide can be used as a catalyst in the dehydration of secondary alcohols. European Patent Specification Publication No. 150,832 also discloses that high purity zirconium oxide, which has a total content of silicon and titanium (expressed as dioxides) of 0.3% by weight or less, is useful as a dehydration catalyst. In addition, European Patent Application Publication No. 0222356 discloses the dehydration of 2-alcohols to terminal olefins using a zirconium oxide catalyst treated with an alkaline solution. Thorium oxide is known as a catalyst for the selective production of the terminal olefin, but its use in industry is difficult because thorium is a radioactive element so that there occurs a serious problem of safety in handling thorium oxide as a catalyst.

Many prior art dehydration catalysts generally suffer from the following disadvantages:

(1) the internal olefin is mainly produced and the selectivity of the terminal olefin is low, especially at high conversion;

(2) the alcohol is converted into a significant amount of ketone (as well as olefin); and/or (3) the catalyst contains a radioactive element so that there is a problem of safety.

A catalyst has now been discovered which overcomes the drawbacks of the prior art dehydration catalysts by providing high selectivity for α-olefins while at the same time eliminating the problems attendant with radioactive materials.

SUMMARY OF THE INVENTION

In accordance with the present invention, there is provided a method of making a hydrous zirconium oxide dehydration catalyst comprising:

A. dissolving zirconyl nitrate in water;

B. hydrolyzing the zirconyl nitrate with ammonia at elevated temperature until substantially all of the zirconyl nitrate is hydrolyzed to hydrous zirconium oxide;

C. recovering the hydrous zirconium oxide and washing it with aqueous ammonium hydroxide until the hydrous zirconium oxide is essentially free of nitrate ions;

D. washing the hydrous zirconium oxide with water until it is essentially free of ammonium ions; and E. drying the resulting product at elevated temperature until it is essentially free of water.

The present invention also provides the product of this process.

There is also provided in accordance with the present invention, a dehydration catalyst comprising hydrous zirconium oxide which is essentially free of nitrate ions, ammonium ions and water.

Further provided in accordance with the present invention is a method for producing a compound having a terminal double bond comprising dehydrating a compound having the general formula

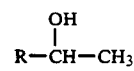

wherein R is a $C_2$–$C_{20}$ hydrocarbon group in the presence of a dehydration catalyst comprising hydrous zirconium oxide which is essentially free of nitrate ions, ammonium ions and water.

DETAILED DESCRIPTION OF PREFERRED EMBODIMENTS

The starting material used in the dehydration method of the present invention is a compound represented by the general formula

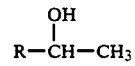
(I)

wherein R is any of $C_2$–$C_{20}$ hydrocarbon groups, which may have double bonds, are preferably $C_2$–$C_{10}$ hydrocarbon groups, more preferably $C_2$–$C_{10}$ saturated hydrocarbon groups. When the present invention is carried out by using such a starting material, a terminal olefin is selectively produced through the elimination of both the hydroxyl and a hydrogen of the methyl shown in formula (I), forming water.

Examples of the compounds represented by formula (I) include, but are not limited to, 1-cyclohexylethanol 4-methyl-2-pentanol and 2-hexanol.

The dehydration catalyst of the present invention is prepared by dissolving zirconyl nitrate in water and hydrolyzing the dissolved zirconyl nitrate with ammonia at an elevated temperature, i.e., about 50° to about 75° C. A precipitate (hydrous zirconium oxide) forms which is recovered and washed thoroughly with aqueous ammonium hydroxide until the precipitate is essentially free of nitrate ions. The precipitate is then washed with water until the precipitate is essentially free of ammonium ions. Finally, the precipitate is dried, e.g., at about 80° C. or higher, preferably under vacuum, until the precipitate is essentially free of water, e.g., for at least about 16 hours. The resulting product is hydrous zirconium oxide which is essentially free of nitrate ions, ammonium ions and water. As used herein, the term "essentially free" means that the catalyst contains about 0.1 wt % or less of the particular material. Before use, the catalyst is calcined at about 350° to about 650° C. for a period of generally about 0.1 to about 50 hours, preferably about 1 to about 10 hours.

It has been found that the catalyst of this invention may be used in admixture with other metal oxides while still achieving high conversion of alcohol to olefin, high selectivity for dehydration, and high selectivity for production of terminal olefin. Thus, the catalyst can contain up to about 15 wt % of a rare earth oxide (such as cerium, ytterium, europium and lanthanum oxide), yttrium oxide or hafnium oxide. On the other hand, some other metal oxides reduce the effectiveness of the catalyst of the present invention. These include titanium, zinc, and indium oxides.

In the present invention, the dehydration reaction is carried out as follows: while the mode of reaction is not particularly restricted, a fixed or fluidized catalyst bed/-vapor-phase reaction system is adopted. The reaction temperature is generally from 200° to 500° C., preferably from 300° to 400° C. The reaction pressure is also not particularly restricted; the reaction can be effected under atmospheric or slightly elevated pressure. If necessary, the vapor of feed compound (I) is diluted with an inert gas such as nitrogen gas before reaction. The reaction under reduced pressure also gives good results. The material feed rate expressed in LHSV is generally from 0.1 to 15 hr$^{-1}$, preferably from 0.5 to 5 hr$^{-1}$.

When the catalyst of the present invention is employed in the dehydration of the above-described alcohols, high conversion of alcohol to olefin, high selectivity for dehydration, and high selectivity for the production of terminal olefin are all achieved. Typically, conversion of at least about 60%, dehydration selectivity of at least about 90% (and often at least 95%), and terminal olefin selectivity of at least about 65% are obtained when the catalyst of this invention are used.

The following examples illustrate the present invention in more detail without limiting the scope of the invention.

COMPARATIVE EXAMPLE A

The following procedure for preparing a zirconium catalyst corresponds to literature descriptions.

Zirconyl nitrate (57.8 g) obtained from J. T. Baker Chemical Co. was mixed with 500 g of distilled water in a creased Morton 1000 mL round-bottom flask fitted with a stirrer, thermometer, and addition funnel. The mixture was stirred vigorously at 25° C. and blanketed with nitrogen. Ammonia (30%, Mallinckrodt, 245 g) was added over a period of 5 minutes and stirring was continued for 15 minutes.

The resulting mixture was placed in two centrifuge bottles and centrifuged at 3000 rpm for 15 minutes. The supernatant liquid was decanted off; 250 mL of distilled water was added to each bottle and mixed thoroughly before centrifuging again. This was repeated five times at which point the wash water was at pH 7.

The precipitate was dried in an oven under nitrogen at 120° C. for 16 hours. The resulting powder was compressed into 10–30 mesh particles to use as a dehydration catalyst.

The catalyst (4 g) was packed in a ½ inch diameter quartz tube and calcined in nitrogen at 600° C. for 4 hours. 2-Hexanol (0.5 mL/hour) was passed over the catalyst at 300° C. in a nitrogen flow of 3 mL/minute for 6 hours. During the last 3 hours of this time, a sample was collected with the results shown in Table A. The conversion and dehydration selectivity were satisfactorily high, but the 1-hexene selectivity was undesirably low.

COMPARATIVE EXAMPLE B AMD EXAMPLES 1 AND 2

Three more experiments using the Baker zirconyl nitrate were made in which the ammonia addition and washing parameters were changed from those used in Comparative Example A. In Comparative Example B, the ammonia addition was conducted at 50° C.; in Example 1, the ammonia addition was also conducted at 50° C., but additional washing of the precipitate first with 15% ammonia and then with water was employed; and in Example 2 the ammonia addition was conducted at 75° C. and the additional washing with ammonia and then water (as in Example 1) was employed. The results of cracking 2-hexanol using these catalysts are indicated in Table A.

EXAMPLE 3

In this experiment, the Baker zirconyl nitrate mixture with water was heated for 1-hour at 50° C. and centrifuged to remove undissolved material before the ammonia addition. Approximately half the material was removed indicating that this source of zirconyl nitrate had already been partially hydrolyzed. Precipitation and washing parameters were as in Example 1. The hydrous oxide obtained was dried at 80° C. under 15 in. Hg vacuum for 16 hours. The derived catalyst gave good results as seen in Table A.

EXAMPLE 4

This experiment was done as in Example 1, except that the zirconyl nitrate which was obtained from Aldrich Chemical Company was fully soluble, and that the hydrous oxide was dried under vacuum.

Aldrich zirconyl nitrate (57.8 g) was dissolved in 250 g of distilled water at 50° C. Ammonia (122 g of 15% ammonia) was added over 30 minutes. The mixture was digested at 50° C. for 90 minutes. The resulting precipitate was first washed with 250 mL of 15% ammonia three times with the last ammonia wash sitting overnight; then with water until the pH reached 7; and then with two more water washes. This final hydrous oxide was divided into two parts as shown in Table A. The first part (Example 4a) was dried under vacuum as in Example 3. The second part (Example 4b) was dried under vacuum at a higher temperature (120° C.) for a longer time (48 hours).

As seen in Table A, both dried oxides gave good cracking results—the first part gave results very similar to Example 3 and the second, which had been more exhaustively dried, gave even better 1-hexene selectivity.

EXAMPLE 5

This experiment was a repeat of Example 4b except that the hydrous oxide was calcined at 550° C. and the cracking was performed at 290° C. The selectivity results shown in Table A were very good.

EXAMPLE 6

This experiment was a repeat of Example 4b except that the precipitate was digested in the ammonia for only 15 minutes instead of 90 minutes.

The cracking results were significantly different. At 300° C., the conversion was very high at 99.9% and dehydration selectivity was very high at 99.8%, but the 1-hexene selectivity was unsatisfactory at only 49%. When the cracking temperature was lowered to 260° C. and conversion dropped to 13%, the dehydration selectivity dropped to an unsatisfactory 91%, while the 1-hexene selectivity was still poor at 59%.

EXAMPLE 7

A similar experiment to Example 4b was run in which the digestion time was 1200 minutes and the drying time was 72 hours. Good cracking results of 94% conversion, 99.5% dehydration selectivity, and 78% 1-hexene selectivity were obtained at 300° C.

TABLE A

| HYDROUS ZIRCONIUM OXIDE PRECIPITATES | | | | |
|---|---|---|---|---|
| CATALYST FROM EXAMPLE | 2-Hexanol Cracking[1] | | | |
| | Temp., °C. | Conversion, % | Dehydration, % | 1-Hexene, % |
| A[2] | 300 | 64 | 98 | 41 |
| B[2] | 300 | 53 | 97.5 | 56 |
| 1[2] | 300 | 88 | 99.2 | 65 |
| 2[2] | 300 | 96 | 98 | 72 |
| 3[3] | 300 | 91 | 97 | 77 |
| 4a[4] | 300 | 99.3 | 98 | 80 |
| 4b[4] | 300 | 84 | 99.5 | 88 |
| 5[4] | 290 | 73 | 99 | 90 |
| 6[4] | 300 | 99.9 | 99.8 | 49 |
| | 260 | 13 | 91 | 59 |
| 7[4] | 300 | 94 | 99.5 | 78 |

[1]Six-hour test, catalyst first calcined 4 hours at 600° C.
[2]Starting material: relatively insoluble ZrO(NO₃)₂ from Baker.
[3]Insoluble ZrO(NO₃)₂ removed before precipitation.
[4]New source of ZrO(NO₃)₂: Aldrich, all soluble.

EXAMPLE 8

Hydrous zirconyl oxide precipitates were prepared in accordance with Example 4b with varying amounts of other metal salts (mainly nitrates) present, thereby preparing the cogel oxides listed in Table B. The results of dehydration reactions using these catalysts are also indicated in Table B.

TABLE B

| HYDROUS ZIRCONIUM OXIDE/METAL OXIDE CATALYSTS | | | | |
|---|---|---|---|---|
| Metal Oxide In Catalyst, Amount | Calcine, temp(°C.) | 2-Hexanol Cracking | | |
| | | Cracking, temp(°C.) | Conversion, % | Dehydration, % | 1-Hexene, % |
| Yttrium oxide, 5 wt % | 600 | 300 | 88 | 96 | 91 |
| Yttrium oxide, 5 wt % | 350 | 300 | 96 | 99 | 77 |
| Yttrium oxide, 5 wt % | 450 | 290 | 97 | 97 | 85 |
| | | 300 | 99 | 96 | 84 |
| Yttrium oxide, 5 wt % | 550 | 290 | 96 | 98.5 | 86 |
| | | 300 | 98 | 96 | 82 |
| Yttrium oxide, 5 wt % | 600[5] | 290 | 99 | 99 | 89 |
| | | 300 | 99 | 98 | 88 |
| Yttrium oxide, 15 wt % | 600 | 300 | 75 | 97.5 | 87 |
| Yttrium oxide, 100 wt %[6] | 600 | 300 | 89 | 90 | 90 |
| Hafnium oxide, 5 wt % | 600 | 300 | 94 | 99 | 83 |
| Cerium oxide, 5 wt % | 600 | 300 | 81 | 99 | 88 |
| Ytterbium oxide, 5 wt % | 600 | 300 | 100 | 99.9 | 76 |
| Europium oxide, 5 wt % | 600 | 300 | 80 | 99.4 | 81 |
| Lanthanum oxide, 15 wt % | 600 | 300 | 99.3 | 95 | 77 |
| Titanium oxide, 5 wt % | 600 | 300 | 86 | 99.8 | 59 |
| Zinc oxide, 5 wt % | 600 | 300 | 99.5 | 32 | 71 |
| Indium oxide, 5 wt % | 600 | 300 | 99 | 13 | 74 |

[5]Calcined in the presence of water.
[6]No hydrous zirconium oxide in catalyst.

The data in Table B shows that the presence of rare earth oxides, yttrium oxide and hafnium oxide in the catalyst does not adversely effect catalyst performance significantly. However, the presence of titanium, zinc and indium oxides does significantly impair catalyst performance.

What is claimed is:

1. A method for producing a compound having a terminal double bond comprising dehydrating a compound having the general formula

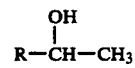

$$\begin{array}{c} \text{OH} \\ | \\ \text{R—CH—CH}_3 \end{array}$$

where R is a $C_2$-$C_{20}$ hydrocarbon group, in the presence of a dehydration catalyst comprising the product produced by the method comprising:

A. dissolving zirconyl nitrate in water;
B. hydrolyzing the zirconyl nitrate with ammonia at elevated temperature until substantially all of the zirconyl nitrate is hydrolyzed to hydrous zirconium oxide;
C. recovering the hydrous zirconium oxide and washing it with aqueous ammonium hydroxide until the hydrous zirconium oxide is essentially free of nitrate ions;
D. washing the hydrous zirconium oxide with water until it is essentially free of ammonium ions; and
E. drying the resulting product at elevated temperature until it is essentially free of water other than water which is chemically bound to the hydrous zirconium oxide.

2. The method claim 1 wherein the dehydration catalyst is calcined prior to its use in the dehydration reaction.

3. The method of claim 1 wherein the compound dehydrated is 2-hexanol and the compound having the terminal double bond is 1-hexene.

4. The method of claim 1 wherein the catalyst further comprises up to about 15 wt % of a rare earth oxide, yttrium oxide or hafnium oxide.

* * * * *